United States Patent

Kameda et al.

[11] 4,082,849
[45] Apr. 4, 1978

[54] HALOGENATED N-(3,5-DIHALOPHENYL)CYCLO-PROPANEDICARBOXIMIDES

[75] Inventors: Nobuyuki Kameda, Takarazuka; Yoshio Hisada, Kawanishi; Toshiro Kato, Ibaraki; Akira Fujinami, Takarazuka, all of Japan

[73] Assignee: Sumitomo Chemical Company, Limited, Japan

[21] Appl. No.: 730,984

[22] Filed: Oct. 8, 1976

[30] Foreign Application Priority Data

Oct. 15, 1975 Japan .................. 50-124670

[51] Int. Cl.$^2$ .................. C07D 209/52; A61K 31/40
[52] U.S. Cl. .................. 424/274; 260/326.5 B
[58] Field of Search .................. 424/274; 260/326.5 B

[56] References Cited

U.S. PATENT DOCUMENTS

| 3,166,571 | 1/1965 | Izzo | 260/326.5 B |
| 3,344,026 | 9/1967 | Greenblatt | 424/274 |
| 3,549,655 | 12/1970 | Bublitz | 260/326.5 B |
| 3,745,170 | 7/1973 | Fujinami | 260/326.5 S |

OTHER PUBLICATIONS

Fujinami et al., Chem. Abs. 75, 5516f (1970).

*Primary Examiner*—R. Gallagher
*Assistant Examiner*—Mark L. Berch
*Attorney, Agent, or Firm*—Birch, Stewart, Kolasch and Birch

[57] ABSTRACT

Novel N-(3,5-dihalophenyl)cyclopropanedicarboximides of the formula:

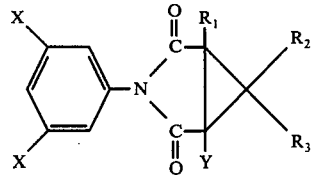

wherein X and Y are each a chlorine atom or a bromine atom and $R_1$, $R_2$ and $R_3$ are individually a hydrogen atom or a methyl group, which show high microbicidal activities against various fungi and bacteria without any material toxicity to mammals and plants and which can be produced by reacting the corresponding cyclopropanedicarboxylic acid or its anhydride with a 3,5-dihaloaniline.

8 Claims, No Drawings

HALOGENATED N-(3,5-DIHALOPHENYL)CYCLOPROPANEDICARBOXIMIDES

The present invention relates to N-(3',5'-dihalophenyl)cyclopropanedicarboximides (hereinafter referred to as "N-(3,5-dihalophenyl)imide(s)") of the formula:

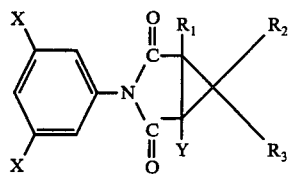

wherein X and Y are each a chlorine atom or a bromine atom and $R_1$, $R_2$ and $R_3$ are individually a hydrogen atom or a methyl group, and their preparation and use.

The N-(3,5-dihalophenyl)imides (I) have prominent effects on such a wide scope of fungi as *Pyricularia oryzae, Sphaerotheca fuliginea, Pellicularia sasakii, Fusarium oxysporum, Sclerotinia sclerotiorum, Corticium rolfsii, Botrytis cinerea, Glomerella cingulata, Rhizoctonia solani, Phytophthora infestans, Rhizopus nigricans, Gibberella fujikuroi, Verticillium albo-atrum* and *Colleto trichum lagenarium*. They can control simultaneously two or more of said fungi and are quite excellent as phytopathogenic microbe-controlling agents. Also, they can effectively control *Aspergillus niger* and *Chaetomium globosum* which propagate in industrial products and hence are excellent as industrial microbicides. Further, they can be readily taken up by roots of plants and immediately translocated to other parts. When applied as soil drench, disease incidence on the aerial parts of plants is prevented. And also, they penetrate into plant tissues from sprayed leaves and prevent disease incidence on plant parts without spray deposit. Spraying thereof on various agricultural and horticultural plants results in no phytotoxicity. Advantageously, they are extremely low in toxicity and have little detrimental actions on mammals and fishes.

A main object of the present invention is to provide novel N-(3,5-dihalophenyl)imides (I), which are useful as microbicides. Another object of this invention is to provide a process for producing such N-(3,5-dihalophenyl)imides (I). A further object of the invention is to provide microbicidal compositions containing such N-(3,5-dihalophenyl)imides (I). These and other objects and advantages of the invention will become apparent from the foregoing and subsequent descriptions.

The N-(3,5-dihalophenyl)imides (I) can be prepared by reacting the corresponding cyclopropanedicarboxylic acid of the formula:

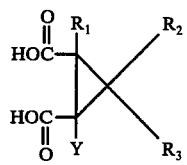

wherein Y, $R_1$, $R_2$ and $R_3$ are each as defined above or its anhydride, with a 3,5-dihaloaniline of the formula:

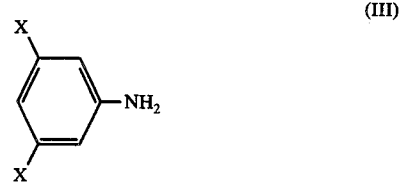

wherein X is as defined above.

Examples of typical procedures for carrying out the said preparation so as to obtain the objective N-(3,5-dihalophenyl)imide (I) in a good yield are as follows:

PROCEDURE A

The cyclopropanedicarboxylic acid (II) or its anhydride is heated with the 3,5-dihaloaniline (III) at a higher temperature (e.g. 150°–250° C), or both of those compounds are heated at a lower temperature (e.g. 70°–150° C) in the presence of a suitable solvent (e.g. benzene, toluene, xylene, chlorobenzene, dichlorobenzene, methyl isobutyl ketone, cyclohexanone) and a catalytic amount of a base (e.g. triethylamine, tributylamine, pyridine, N-methylmorpholine, potassium carbonate, sodium carbonate, sodium acetate) to give the N-(3,5-dihalophenyl)imide (I).

PROCEDURE B

The anhydride of the cyclopropanedicarboxylic acid (II) is reacted with the 3,5-dihaloaniline (III) in the presence of a suitable solvent (e.g. benzene, toluene, xylene, tetrahydrofuran, dioxane, isopropyl ether, chlorobenzene) and then the resulting cyclopropanedicarboxylic acid monoamide is dehydrated in the presence of a suitable dehydrating agent (e.g. acetic anhydride, phosphorus pentoxide, phosphorus oxychloride, acetyl chloride, thionyl chloride) to give the N-(3,5-dihalophenyl)imide (I).

The N-(3,5-dihalophenyl)imide (I) thus produced may be purified, if necessary, by a per se conventional procedure such as recrystallization from a proper solvent.

The starting cyclopropanedicarboxylic acid (II) or its anhydride can be produced, for instance, by the process as described in L. L. McCoy, J.Org.Chem., 25, 2078–2082 (1960).

In actual application as microbicides, the N-(3,5-dihalophenyl)imides (I) may be used alone without incorporation of any other ingredients such as carriers and diluents or, for easier application, in admixture with such solid carriers or diluents as talc, clay and the like or with such liquid carriers or diluents as organic solvents and the like. The microbicidal compositions can be formulated into any of the ordinarily adopted forms such as, for example, dusts, wettable powders, oil sprays, aerosols, tablets, emulsifiable concentrates and granules.

Further, the N-(3,5-dihalophenyl)imides (I) may be used in admixture with other chemicals such as, for example, Blasticidin S, Kasugamycin, Polyoxin, acetylene dicarboximide, 3-[2-(3,5-dimethyl-2-oxocyclohexyl)-2-hydroxyethyl]-glutarimide, streptomycin, griseofluvin, pentachloronitrobenzene, pentachlorophenol, hexachlorobenzene, pentachlorobenzyl alcohol, pentachlorobenzaldoxime, 2,6-dichloro-4-nitroaniline, zinc ethylene bisdithiocarbamate, zinc dimethyl thiocarbamate, manganese ethylene bisdithiocarbamate, bis(- dimethylthiocarbamoyl) disulfide, 2,4,5,6-tetrachloroisophthalonitrile, 2,3-dichloro-1,4-naphthoquinone, tetrachloro-p-benzoquinone, p-dimethylaminobenzenediazo sodium sulfonate, 2-(1-methylheptyl)-4,6-dinitrophenyl crotonate, 2-heptadecylimidazoline acetate, 2,4-dichloro-6-(o-chloroanilino)-S-triazine, dodecylguanidine acetate, 6-methyl-2,3-quinoxalinedithiol cyclic-S,S-dithiocarbonate, 2,3-quinoxalinedithiol cyclic trithiocarbonate, N-trichloromethylthio-4-cyclohexene-1,2-dicarboximide, N-(1,1,2,2-tetrachloroethylthio)-4-cyclohexene-1,2-dicarboximide, N-(3,5-dichlorophenyl)maleinimide, N-(3,5-dichlorophenyl)succinimide, N-(3,5-dichlorophenyl)itaconimide, 3-(3',5'-dichlorophenyl)-5,5-dimethyloxazolidine-2,4-dione, 2,3-dihydro-5-carboxanilide-6-methyl-1,4-oxazine-4,4-dioxide, 2,3-dihydro-5-carboxanilide-6-methyl-1,4-oxazine, 1-(N-n-butylcarbamoyl)-2-methoxycarbonylaminobenzimidazole, α-cyano-3-phenoxybenzyl 2-(4-chlorophenyl) isovalerate, 3-phenoxybenzyl 2,2-dimethyl-3-(2',2'-dichlorovinyl)-cyclopropanecarboxylate, 3-phenoxybenzyl chrysanthemate, 2-methoxy-4H-1,3,2-benzodioxaphospholine-2-sulfide, p-cyanobenzyl dimethyl phosphorothionate, 0,0-diethyl-S-benzyl phosphorothioate, 0-ethyl-S,S-diphenyl phosphorodithioate, 0-ethyl-0-phenyl-0-(2,4,5-trichlorophenyl) phosphate, 0,0-dimethyl-0-(3-methyl-4-nitrophenyl) phosphorothioate, S-[1,2-bis(ethoxycarbonyl)-ethyl]-0,0-dimethyl phosphorodithioate, 0,0-dimethyl-S-(N-methylcarbamoylmethyl) phosphorodithioate, 0,0-diethyl-0-(2-isopropyl-6-methyl-4-pyrimidyl) thiophosphate, 3,4-dimethylphenyl-N-methylcarbamate, iron methylarsonate, 2-chloro-4,6-bis(ethylamino)-S-triazine, 2,4-dichlorophenoxyacetic acid (including its salts and esters), 2-methyl-4-chlorophenoxyacetic acid (including its salts and esters), 2,4-dichlorophenyl-4'-nitrophenyl ether, sodium pentachlorophenolate, N-(3,4-dichlorophenyl) propionamide, 3-(3',4'-dichlorophenyl)-1,1-dimethylurea, α,α,α-trifluoro-2,6-dinitro-N,N-di-n-propyl-p-toluidine, 2-chloro-2',6'-diethyl-N-(methoxymethyl) acetamide, 1-naphthyl-N-methylcarbamate, methyl-N-(3,4-dichlorophenyl) carbamate, 4-chlorobenzyl-N,N-dimethylthiol carbamate, N,N-diallyl-2-chloroacetamide, ethyl-β-(2,4-dichlorophenoxy) acrylate and cyclohexyl-β-(2,4-dichlorophenoxy) acrylate; and, in every case, no controlling effects of the individual chemicals are decreased. Accordingly, simultaneous control of two or more pests and injurious insects is possible. In addition thereto, they may be used in admixture with such agricultural chemicals as insecticides and miticides and with fertilizers.

Practical and presently preferred embodiments of the present invention are illustratively shown in the following examples, wherein parts and % are by weight.

EXAMPLE 1

Preparation of the N-(3,5-dihalophenyl)imides (I)

Procedure A

In a 100 ml volume four necked flask equipped with a water separator, a mixture containing 8.9 g of α-chloro-β-methylcyclopropanedicarboxylic acid, 8.1 g of 3,5-dichloroaniline, 0.5 g of triethylamine and 50 ml of xylene was refluxed for 3 hours. After removal of the solvent, the residue was recrystallized from n-hexane-benzene to give 12.4 g of N-(3,5-dichlorophenyl)-α-chloro-β-methylcyclopropanedicarboximide. M.P. 172.5°–173.5° C. Anal. Calcd. for $C_{12}H_8NCl_3O_2$: C, 47.32; H, 2.65; N, 4.60; Cl, 34.92. Found: C, 47.49; H, 2.79; N, 4.72; Cl, 35.13.

Procedure B

A mixture containing 8.0 g of α-chloro-β-methylcyclopropanedicarboxylic anhydride, 12.5 g of 3,5-dibromoaniline and 100 ml of toluene was refluxed for 1 hour. After cooling, the resulting mixture was admixed with 20 g of acetic anhydride and 0.5 g of sodium acetate, refluxed for 1 hour and poured into 100 ml of water. The precipitate was filtered, washed with water and dried in vacuum to give 15.6 g of N-(3,5-dibromophenyl)-α-chloro-β-methylcyclopropanedicarboximide. M.P. 189.0°–190.0° C. Anal. Calcd. for $C_{12}H_8NBr_2ClO_2$: C, 36.63; H, 2.05; N, 3.56. Found: C, 36.48; N, 2.25; N, 3.50.

In the same manner as above, the N-(3,5-dihalophenyl)imides (I) as shown in Table 1 were prepared:

Table 1

| Starting materials | | Produced N-(3,5-dihalophenyl)cyclopropanedicarboximides (I) | | | | | | | | |
|---|---|---|---|---|---|---|---|---|---|---|
| Cyclopropane-dicarboxylic acid or its anhydride (II) | 3,5-Dihalo-aniline (III) | Procedure | No. | Chemical structure | Melting point (° C) | Yield (%) | Elementary analysis (%) | | | |
| | | | | | | | C | H | N | Halogen |
| Cl–COOH / COOH / CH₃ | Cl / NH₂ / Cl | A | 1 | (structure) | 172.5–173.5 | 82 | 47.32 (47.49) | 2.65 (2.79) | 4.60 (4.72) | (Cl) 34.92 (35.13) |
| Cl–COOH / COOH | Cl / NH₂ / Cl | A | 2 | (structure) | 142.0–143.0 | 84 | 45.74 (45.33) | 2.09 (1.92) | 4.82 (4.79) | (Cl) 36.61 (36.68) |

Table 1-continued

| Starting materials | | | Produced N-(3,5-dihalophenyl)cyclopropanedicarboximides (I) | | | | | | | |
|---|---|---|---|---|---|---|---|---|---|---|
| Cyclopropane-dicarboxylic acid or its anhydride (II) | 3,5-Dihalo-aniline (III) | Proce-dure | No. | Chemical structure | Melting point (°C) | Yield (%) | \multicolumn{4}{c}{Elementary analysis (%)} |
| | | | | | | | C | H | N | Halogen |
| (structure with Cl, CO, O, CO, CH₃) | (structure with Br, Br, NH₂) | B | 3 | (structure with Br, Br, N, C=O, Cl, CH₃) | 189.0–190.0 | 80 | 36.63 (36.48) | 2.05 (2.25) | 3.56 (3.50) | |
| (structure with Cl, CO, O, CO, CH₃) | (structure with Cl, Cl, NH₂) | B | 4 | (structure with Cl, Cl, N, C=O, Cl, CH₃) | 168.0–171.5 | 77 | 47.32 (47.50) | 2.65 (2.56) | 4.60 (4.37) | (Cl) 34.92 |
| (structure with Br, CO, O, CO, CH₃) | (structure with Cl, Cl, NH₂) | A | 5 | (structure with Cl, Cl, N, C=O, Br, CH₃) | 178.5–181.5 | 79 | 47.30 (47.52) | 2.31 (2.18) | 4.01 (4.25) | |

EXAMPLE 2

Formulation of Compositions a. Dust

2 Parts of the compound (1) and 98 parts of clay were thoroughly pulverized and mixed together to obtain a dust containing 2% of the active ingredient. In application, the dust was dusted as such.

b. Dust

2 Parts of the compound (5) and 98 parts of talc were thoroughly pulverized and mixed together to obtain a dust containing 2% of the active ingredient. In application, the dust was dusted as such.

c. Wettable powder

50 Parts of the compound (4), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting solution was sprayed.

d. Emulsifiable concentrate

10 Parts of the compound (3), 80 parts of dimethyl sulfoxide and 10 parts of an emulsifier of the polyoxyethylene phenylphenol ether type were mixed together to obtain an emulsifiable concentrate containing 10% of the active ingredient. In application, the emulsifiable concentrate was diluted with water, and the resulting emulsion was sprayed.

e. Granule

5 Parts of the compound (2), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the N-(3,5-dihalophenyl)imides (I). In these examples, the compound numbers correspond to those in Table 1.

EXAMPLE 3

Test for *Rhizoctonia solani* controlling effect on cucumber

Farm soil was charged into pots of 9 cm in diameter and a soil (10 ml) infected with *Rhizoctonia solani* was dispersed over the surface of said soil. Each of the test compounds in the form of emulsifiable concentrates was diluted with water to a given concentration, and the dilution was applied into each pot in a proportion of 20 ml per pot. After 2 hours, 10 seeds of cucumber were sowed therein. 5 Days thereafter, the infectious state of the grown seedlings was observed, and the percentage of stand was calculated according to the following equation:

$$\text{Percentage of stand (\%)} = \frac{\text{Number of healthy seedlings in treated plot}}{\text{Number of germinated seedlings in untreated and uninoculated plot}} \times 100$$

The results are shown in Table 2.

Table 2

| No. | Compound | Concentration (ppm) | Percentage of stand (%) |
|---|---|---|---|
| 1 | (structure: 3,5-dichlorophenyl-N-cyclopropanedicarboximide with CH₃) | 500 / 250 | 100 / 100 |
| 2 | (structure: 3,5-dichlorophenyl-N-cyclopropanedicarboximide) | 500 / 250 | 100 / 100 |

Table 2-continued

| No. | Compound | Concentration (ppm) | Percentage of stand (%) |
|---|---|---|---|
| 4 | [3,5-dichlorophenyl-N-substituted cyclopropane dicarboximide with CH$_3$] | 500 / 250 | 100 / 96.7 |
| *) | [3,5-dichlorophenyl-N-substituted with two CH$_3$ groups] | 500 / 250 | 21.3 / 0 |
| **) | [pentachloronitrobenzene structure] | 250 | 93.4 |
| — | Untreated (inoculated) | — | 0 |
| — | Untreated (uninoculated) | — | 100.0 |

Note:
*) Known fungicide as described in U.S. Pat. 3,745,170.
**) Commercially available fungicide ("PCNB").

EXAMPLE 4

Test for *Glomerella Cingulata* controlling effect on grape

An aqueous dilution of the test compound in the form of a wettable powder preparation was applied to berries of grape at a rate of 20 ml per branch. After one day, *Glomerella cingulata* was inoculated on the surface of the berries immediately after injuring the inoculation site. Three days after inoculation, disease assessment was made. Percentage of control was calculated from the diameter of diseased area according to the following equation:

$$\text{Percentage of control (\%)} = \left\{ 1 - \frac{\text{Mean diameter of diseased area in treated plot}}{\text{Mean diameter of diseased area in untreated plot}} \right\} \times 100$$

The results are shown in Table 3.

Table 3

| No. | Compound | Concentration of ingredient (ppm) | Percentage of control (%) |
|---|---|---|---|
| 1 | [3,5-dichlorophenyl-N-cyclopropane dicarboximide with CH$_3$] | 250 | 100 |
| 2 | [3,5-dichlorophenyl-N-cyclopropane dicarboximide with Cl] | 250 | 100 |
| 3 | [3,5-dibromophenyl-N-cyclopropane dicarboximide with Cl and CH$_3$] | 250 | 78.5 |
| *) | [3,5-dichlorophenyl-N-cyclopropane dicarboximide with two CH$_3$] | 250 | 6.5 |
| **) | Mancozeb | 140 | 65.0 |
| — | Untreated | — | 0 |

Note:
*) Known fungicide as described in U.S. Pat. 3,745,170.
**) Commercially available fungicide.

EXAMPLE 5

Test for *Botrytis cinerea* controlling effect on cucumbers

An aqueous dilution of the test compound in the form of a wettable powder preparation was applied to cotyledons of cucumbers, grown in pots of 9 cm in diameter, at a rate of 7 ml per pot. After one day, agar discs (diameter: 5 mm) with *Botrytis cinerea* were put on the leaves for inoculation. Three days after, the disease severity was observed, and the disease-controlling effect was estimated.

Percentage of control was determined by the following procedure. The rate of diseased area on the tested leaf was measured and classified in one of the six infectious indexes (0, 1, 2, 3, 4, 5) according to the undermentioned criteria. The number of leaves corresponding to each infectious index ($n_0$, $n_1$, $n_2$, $n_3$, $n_4$, $n_5$) was determined, and percentage of control was calculated according to the undermentioned equation:

| Infectious index | Rate of diseased area |
|---|---|
| 0 | No diseased spot |
| 1 | Diseased spot directly under or around inoculated spot |
| 2 | Diseased spot in about 1/5 of leaf area |
| 3 | Diseased spot in about 2/5 of leaf area |
| 4 | Diseased spot in about 3/5 of leaf area |
| 5 | Diseased spot in more than 3/5 of leaf area |

Percentage of control (%) =

$$\left\{ 1 - \frac{0 \times n_0 + 1 \times n_1 + 2 \times n_2 + 3 \times n_3 + 4 \times n_4 + 5 \times n_5}{5 \times n} \right\} \times 100$$

The results are shown in Table 4.

Table 4

| No. | Compound | Concentration (ppm) | Percentage of control (%) |
|-----|----------|---------------------|---------------------------|
| 1 | [Structure: 3,5-dichlorophenyl-N-imide with cyclopropane-CH₃] | 200 / 50 | 100 / 100 |
| 2 | [Structure: 3,5-dichlorophenyl-N-imide with Cl on cyclopropane] | 200 / 50 | 100 / 100 |
| 3 | [Structure: 3,5-dibromophenyl-N-imide with Cl-cyclopropane-CH₃] | 200 / 50 | 100 / 92 |
| 4 | [Structure: 3,5-dichlorophenyl-N-imide with Cl-cyclopropane-CH₃] | 200 / 50 | 100 / 100 |
| 5 | [Structure: 3,5-dichlorophenyl-N-imide with Br-cyclopropane-CH₃] | 200 / 50 | 100 / 95 |
| *) | Methyl-1-(butylcarbamoyl)-2-benzimidazole carbamate | 200 / 50 | 100 / 90 |
| — | Untreated | — | 0 |

Note:
*) Commercially available fungicide ("Benomyl").

EXAMPLE 6

Test for *Sclerotinia sclerotiorum* controlling effect on cucumbers

An aqueous dilution of the test compound in the form of a wettable powder preparation was applied to cucumbers at the first leaf stage, grown in pots of 9 cm in diameter, at a rate of 7 ml per pot. After one day, *Sclerotinia sclerotiorum* was inoculated on the surface of the leaf, and the disease severity was observed three days thereafter. The percentage of control was determined in the following manner. The rate of diseased area on the leaf was measured and classified in one of the six infectious indexes (0, 1, 2, 3, 4, 5) according to the undermentioned criteria. The number of leaves corresponding to each infectious index ($n_0$, $n_1$, $n_2$, $n_3$, $n_4$, $n_5$) was determined, and the percentage of control was calculated according to the undermentioned equation:

| Infectious index | Rate of diseased area |
|------------------|----------------------|
| 0 | No diseased spot |
| 1 | Diseased spot directly under or around inoculated spot |
| 2 | Diseased spot in about 1/5 of leaf area |
| 3 | Diseased spot in about 2/5 of leaf area |
| 4 | Diseased spot in about 3/5 of leaf area |
| 5 | Diseased spot in more than 3/5 of leaf area |

Percentage of control (%) =

$$\left\{1 - \frac{0 \times n_0 + 1 \times n_1 + 2 \times n_2 + 3 \times n_3 + 4 \times n_4 + 5 \times n_5}{5 \times n}\right\} \times 100$$

The results are shown in Table 5.

Table 5

| No. | Compound | Concentration (ppm) | Percentage of control |
|-----|----------|---------------------|----------------------|
| 1 | [Structure: 3,5-dichlorophenyl-N-imide with Cl-cyclopropane-CH₃] | 100 | 100 |
| 2 | [Structure: 3,5-dichlorophenyl-N-imide with Cl-cyclopropane] | 100 | 100 |
| 3 | [Structure: 3,5-dibromophenyl-N-imide with Cl-cyclopropane-CH₃] | 100 | 94 |
| 4 | [Structure: 3,5-dichlorophenyl-N-imide with Cl-cyclopropane-CH₃] | 100 | 100 |
| 5 | [Structure: 3,5-dichlorophenyl-N-imide with Br-cyclopropane-CH₃] | 100 | 100 |
| *) | Methyl-1-(butylcarbamoyl)-2-benzimidazole carbamate | 100 | 35 |
| — | Untreated | — | 0 |

Note:
*) Commercially available fungicide.

EXAMPLE 7

Anti-fungal Spectrum

By means of the agar dilution method, the growth inhibiting effects of the N-(3,5-dihalophenyl)imides (I) on various phytopathogenic fungi and parasites of industrial products were investigated. The PSA plate which contained the test compound at 50 ppm of final concentration was inoculated by placing a 5 mm agar disc with growing mycelium and incubated at 28° C. Two to 7 days after inoculation, the diameter of mycelial colony was measured on the basis of the following criteria:

A: No growth
B: 90 % inhibition
C: 70 % inhibition
D: 30 % inhibition
E: 5 % inhibition
F: No inhibition wherein X and Y are each a chlorine atom or a bromine atom and $R_1$, $R_2$ and $R_3$ are individually a hydrogen atom or a methyl group.

2. The compound according to claim 1, wherein X is a chlorine atom.

3. The compound according to claim 1, wherein each of X and Y is a chlorine atom or a bromine atom, $R_1$ is a methyl group and each of $R_2$ and $R_3$ is a hydrogen atom.

4. The compound according to claim 1, wherein each of X and Y is a chlorine atom, $R_1$ is a methyl group and Table 6

| Test fungi | Compound No. 1 | No. 3 | *) |
|---|---|---|---|
| Phytophthora infestans | A | A | F |
| Rhizopus nigricans | A | B | F |
| Pyricularia oryzae | B | B | F |
| Pellicularia sasakii | A | A | A |
| Botrytis cinerea | A | A | A |
| Sclerotinia Sclerotiorum | A | A | A |
| Glomerella cingulata | A | A | D |
| Rhizoctonia solani | A | A | B |
| Giberella fujikuroi | A | A | F |
| Corticium rolfsii | A | A | F |
| Verticillium albo-atrum | A | A | E |
| Fusarium oxysporum f. lycopersici | A | A | C |
| Colletotrichum lagenarium | A | B | F |
| Aspergillus niger ATCC 6275 | A | A | E |
| Chaetomium globosum ATCC 6205 | A | A | E |

Note:
*) Known fungicide as described in U.S. Pat. 3,745,170.

What is claimed is:
1. A compound of the formula:

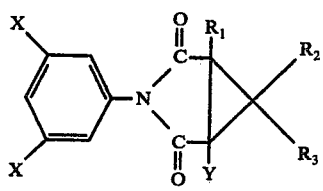

each of $R_2$ and $R_3$ is a hydrogen atom.

5. The compound according to claim 1, wherein each of X and Y is a chlorine atom, $R_2$ is a hydrogen atom or a methyl group and each of $R_1$ and $R_3$ is a hydrogen atom.

6. A method for controlling fungi which comprises applying a fungicidally effective amount of the compound according to claim 1 to the fungi.

7. A microbicidal composition which comprises a microbicidally effective amount of the compound according to claim 1 and an inert carrier.

8. The microbicidal composition according to claim 7, which is in the form of a dust, wettable powder, emulsifiable concentrate, granule, oil spray or aerosol.